(12) United States Patent
Wisman et al.

(10) Patent No.: US 11,268,151 B2
(45) Date of Patent: Mar. 8, 2022

(54) BIOMARKERS FOR CERVICAL CANCER

(71) Applicants: Rijksuniversiteit Groningen, Groningen (NL); Academisch Ziekenhuis Groningen, Groningen (NL)

(72) Inventors: Gijsbertha Barendina Alida Wisman, Groningen (NL); Ate Gerard Jan van der Zee, Groningen (NL); Eduardus Maria Dominicus Schuuring, Groningen (NL)

(73) Assignees: Rijksuniversiteit Groningen, Groningen (NL); Academisch Ziekenhuis Groningen, Groningen (NL)

( * ) Notice: Subject to any disclaimer, the term of this patent is extended or adjusted under 35 U.S.C. 154(b) by 26 days.

(21) Appl. No.: 15/511,767

(22) PCT Filed: Sep. 21, 2015

(86) PCT No.: PCT/NL2015/050650
§ 371 (c)(1),
(2) Date: Mar. 16, 2017

(87) PCT Pub. No.: WO2016/048138
PCT Pub. Date: Mar. 31, 2016

(65) Prior Publication Data
US 2017/0240974 A1    Aug. 24, 2017

(30) Foreign Application Priority Data

Sep. 22, 2014  (EP) ..................................... 14185831

(51) Int. Cl.
*C12Q 1/6886* (2018.01)
*C12Q 1/70* (2006.01)

(52) U.S. Cl.
CPC .......... *C12Q 1/6886* (2013.01); *C12Q 1/708* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

2013/0116144 A1   5/2013  An et al.

FOREIGN PATENT DOCUMENTS

| EP | 2177615 A1 | 4/2010 | |
| WO | WO-9947706 A1 * | 9/1999 | .......... C12Q 1/6874 |
| WO | 2009/115615 A2 | 9/2009 | |

(Continued)

OTHER PUBLICATIONS

Farkas, S.A. et al. Epigenetics 8(11):1213 (Sep. 2013).*

(Continued)

*Primary Examiner* — Diana B Johannsen
(74) *Attorney, Agent, or Firm* — Banner & Witcoff, Ltd.

(57) ABSTRACT

The invention relates to methods, reagents and kits for detecting the susceptibility to cervical cancer. In particular, it relates to novel methylation markers to improve screening for cervical intraepithelial neoplasia grade 2/3 (CIN2/3) and the use thereof for identifying a cervical cell as neoplastic or predisposed to neoplasia in an isolated sample.

16 Claims, 6 Drawing Sheets

Figure 1:
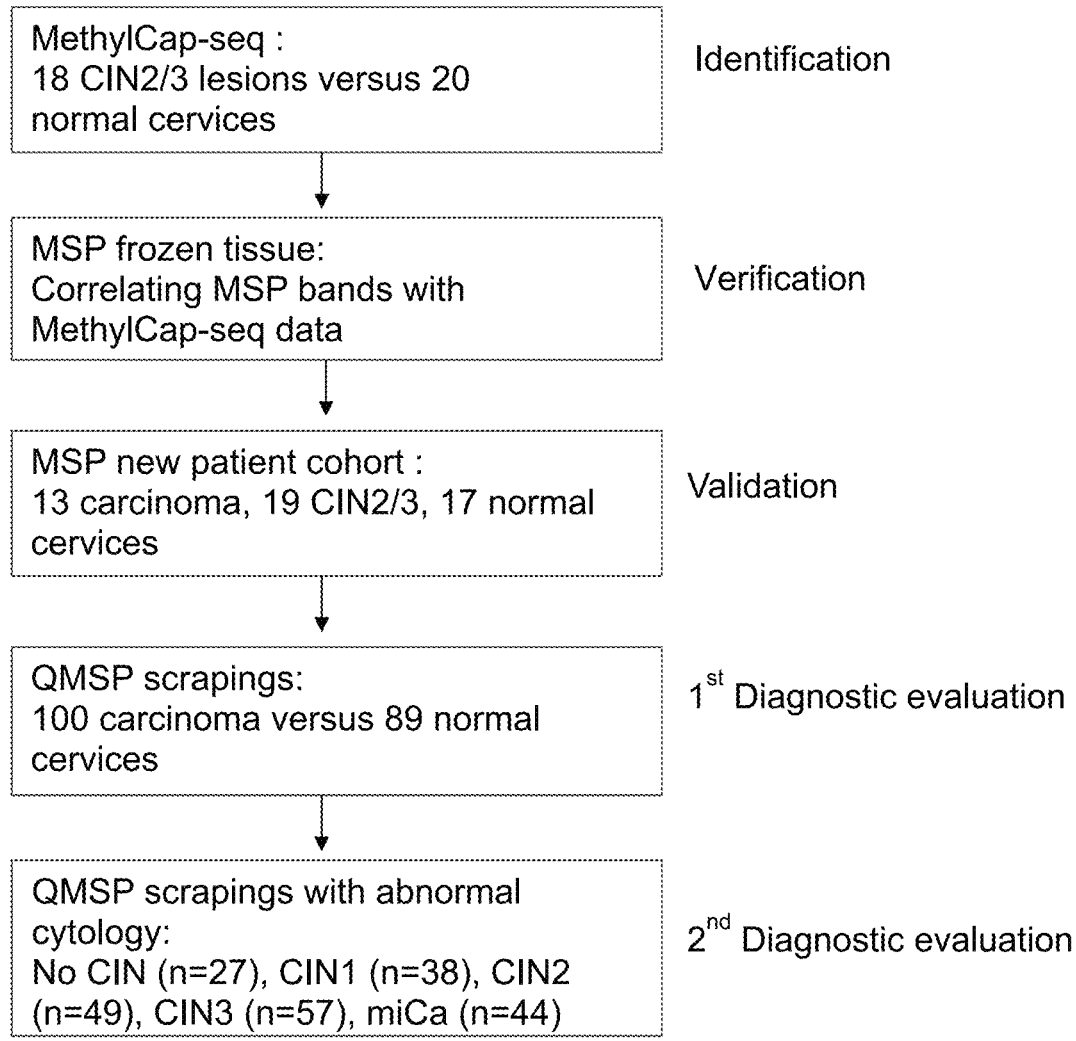

Specification includes a Sequence Listing.

(56) References Cited

FOREIGN PATENT DOCUMENTS

WO       2011/036173 A1     3/2011
WO       2012/104642 A1     8/2012

OTHER PUBLICATIONS

Boers, A. et al. Clinical Epigenetics 8:29 (2016).*
Hoque, M.O. et al. Cancer Research 68(8):2661 (Apr. 2008). (Year: 2008).*
J.J.H. Eijsink et al: "A four-gene methylation marker panel as triage test in high-risk human papillomavirus positive patients", International Journal of Cancer, vol. 130, No. 8, Feb. 13, 2012 (Feb. 13, 2012), pp. 1861-1869, XP055180403, ISSN: 0020-7136, DOI: 10.1002/ijc.26326.
Bodi L Oster et al: "Identification and validation of highly frequent CpG island hypermethylation in colorectal adenomas and carcinomas", International Journal of Cancer, vol. 129, No. 12, Dec. 15, 2011 (Dec. 15, 2011), pp. 2855-2866, XP055036667, ISSN: 0020-7136, DOI: 10.1002/ijc.25951.
Boers, A., et al.,"DNA methylation analysis in self-sampled brush material as a triage test in hrHPV-positive women," British Journal of Cancer, Sep. 9, 2014, pp. 1095-1101, vol. 111, No. 6.
Roessler et al., "Quantitative cross-validation and content analysis of the 450k DNA methylation array from Illumina, Inc.," BMC Research Notes, 2012, vol. 5:210.

* cited by examiner

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial
<220> FEATURE:
<223> OTHER INFORMATION: ZSCAN1 forward primer

<400> SEQUENCE: 1
ttgttggtat tcgtttgttc                                            20

<210> SEQ ID NO 2
<211> LENGTH: 18
<212> TYPE: DNA
<213> ORGANISM: ARTIFICIAL
<220> FEATURE:
<223> OTHER INFORMATION: ZSCAN1 REVERSE PRIMER

<400> SEQUENCE: 2
```

```
acgcgaccga acgatatt                                                  18

<210> SEQ ID NO 3
<211> LENGTH: 20
<212> TYPE: DNA
<213> ORGANISM: ARTIFICIAL
<220> FEATURE:
<223> OTHER INFORMATION: ST6GALNAC5 FORWARD PRIMER

<400> SEQUENCE: 3
gtagttgcgg atggaggttc                                                20

<210> SEQ ID NO 4
<211> LENGTH: 20
<212> TYPE: DNA
<213> ORGANISM: ARTIFICIAL
<220> FEATURE:
<223> OTHER INFORMATION: ST6GALNAC5 REVERSE PRIMER

<400> SEQUENCE: 4
ctaactacgc tcaccctccg                                                20

<210> SEQ ID NO 5
<211> LENGTH: 20
<212> TYPE: DNA
<213> ORGANISM: ARTIFICIAL
<220> FEATURE:
<223> OTHER INFORMATION: ANKRD18CP FORWARD PRIMER

<400> SEQUENCE: 5
cgatgtggta ttttcgattc                                                20

<210> SEQ ID NO 6
<211> LENGTH: 19
<212> TYPE: DNA
<213> ORGANISM: ARTIFICIAL
<220> FEATURE:
<223> OTHER INFORMATION: ANKRD18CP REVERSE PRIMER

<400> SEQUENCE: 6
acgtctaaaa aatcgccac                                                 19

<210> SEQ ID NO 7
<211> LENGTH: 16
<212> TYPE: DNA
<213> ORGANISM: ARTIFICIAL
<220> FEATURE:
<223> OTHER INFORMATION: CDH6 FORWARD PRIMER

<400> SEQUENCE: 7
gggcggcgtt gttgtc                                                    16

<210> SEQ ID NO 8
<211> LENGTH: 18
<212> TYPE: DNA
<213> ORGANISM: ARTIFICIAL
<220> FEATURE:
<223> OTHER INFORMATION: CDH6 REVERSE PRIMER

<400> SEQUENCE: 8
ccaaccccac gacgaatc                                                  18

<210> SEQ ID NO 9
<211> LENGTH: 19
<212> TYPE: DNA
<213> ORGANISM: ARTIFICIAL
```

```
<220> FEATURE:
<223> OTHER INFORMATION: GFRA1 FORWARD PRIMER

<400> SEQUENCE: 9
tagggggaat cgatgtttc                                                  19

<210> SEQ ID NO 10
<211> LENGTH: 20
<212> TYPE: DNA
<213> ORGANISM: ARTIFICIAL
<220> FEATURE:
<223> OTHER INFORMATION: GFRA1 REVERSE PRIMER

<400> SEQUENCE: 10
gaatcctaaa caccgaacga                                                 20

<210> SEQ ID NO 11
<211> LENGTH: 18
<212> TYPE: DNA
<213> ORGANISM: ARTIFICIAL
<220> FEATURE:
<223> OTHER INFORMATION: GATA4 FORWARD PRIMER

<400> SEQUENCE: 11
ggtcgggtta attcggtc                                                   18

<210> SEQ ID NO 12
<211> LENGTH: 20
<212> TYPE: DNA
<213> ORGANISM: ARTIFICIAL
<220> FEATURE:
<223> OTHER INFORMATION: GATA4 REVERSE PRIMER

<400> SEQUENCE: 12
cctcgacaaa actcaaaacg                                                 20

<210> SEQ ID NO 13
<211> LENGTH: 20
<212> TYPE: DNA
<213> ORGANISM: ARTIFICIAL
<220> FEATURE:
<223> OTHER INFORMATION: KCNIP4 FORWARD PRIMER

<400> SEQUENCE: 13
gggacgtagg gtgtagaagc                                                 20

<210> SEQ ID NO 14
<211> LENGTH: 18
<212> TYPE: DNA
<213> ORGANISM: ARTIFICIAL
<220> FEATURE:
<223> OTHER INFORMATION: KCNIP4 REVERSE PRIMER

<400> SEQUENCE: 14
aaactctcgc tcccaacg                                                   18

<210> SEQ ID NO 15
<211> LENGTH: 20
<212> TYPE: DNA
<213> ORGANISM: ARTIFICIAL
<220> FEATURE:
<223> OTHER INFORMATION: LHX8 FORWARD PRIMER

<400> SEQUENCE: 15
tatttttttc gtagcggatc                                                 20
```

```
<210> SEQ ID NO 16
<211> LENGTH: 20
<212> TYPE: DNA
<213> ORGANISM: ARTIFICIAL
<220> FEATURE:
<223> OTHER INFORMATION: LHX8 REVERSE PRIMER

<400> SEQUENCE: 16
acgaaaaacc aaattctacg                                              20

<210> SEQ ID NO 17
<211> LENGTH: 38
<212> TYPE: DNA
<213> ORGANISM: ARTIFICIAL
<220> FEATURE:
<223> OTHER INFORMATION: ZSCAN1 PROBE

<400> SEQUENCE: 17
aggtcgaagt tttttacgt atttttattg ttcgttta                           38

<210> SEQ ID NO 18
<211> LENGTH: 28
<212> TYPE: DNA
<213> ORGANISM: ARTIFICIAL
<220> FEATURE:
<223> OTHER INFORMATION: ST6GALNAC5 PROBE

<400> SEQUENCE: 18
ttgaagtttc gggtttggtc gtcgagtc                                     28

<210> SEQ ID NO 19
<211> LENGTH: 27
<212> TYPE: DNA
<213> ORGANISM: ARTIFICIAL
<220> FEATURE:
<223> OTHER INFORMATION: ANKRD18CP PROBE

<400> SEQUENCE: 19
aggagcgttt ggtttaggcg tttttcg                                      27

<210> SEQ ID NO 20
<211> LENGTH: 33
<212> TYPE: DNA
<213> ORGANISM: ARTIFICIAL
<220> FEATURE:
<223> OTHER INFORMATION: CDH6 PROBE

<400> SEQUENCE: 20
cgtttttcgg ggagtttggg tatcgttttt tcg                               33

<210> SEQ ID NO 21
<211> LENGTH: 22
<212> TYPE: DNA
<213> ORGANISM: ARTIFICIAL
<220> FEATURE:
<223> OTHER INFORMATION: GFRA1 PROBE

<400> SEQUENCE: 21
tttattcgtc gcgcgttttc gg                                           22

<210> SEQ ID NO 22
<211> LENGTH: 23
<212> TYPE: DNA
<213> ORGANISM: ARTIFICIAL
<220> FEATURE:
<223> OTHER INFORMATION: GATA4 PROBE
```

```
<400> SEQUENCE: 22
atttcggtga gtaggagcgc gag                                              23

<210> SEQ ID NO 23
<211> LENGTH: 34
<212> TYPE: DNA
<213> ORGANISM: ARTIFICIAL
<220> FEATURE:
<223> OTHER INFORMATION: KCNIP4 PROBE

<400> SEQUENCE: 23
tcggttaggg gcgtttgttt acgggtttgt acgg                                  34

<210> SEQ ID NO 24
<211> LENGTH: 20
<212> TYPE: DNA
<213> ORGANISM: ARTIFICIAL
<220> FEATURE:
<223> OTHER INFORMATION: LHX8 PROBE

<400> SEQUENCE: 24
attggcgttt tgcgaatcgg                                                  20
```

BIOMARKERS FOR CERVICAL CANCER

The invention relates to methods, reagents and kits for detecting the susceptibility to cervical cancer. In particular, it relates to novel methylation markers to improve screening for cervical intraepithelial neoplasia grade 2/3 and the use thereof for identifying a cervical cell as neoplastic or predisposed to neoplasia in an isolated sample.

Cervical cancer is characterized by a well-defined premalignant phase, cervical intraepithelial neoplasia (CIN). Identification of these CIN lesions by population-based screening programs and their subsequent treatment has led to a significant reduction of the incidence and mortality of cervical cancer[1,2]. Cytology-based testing of cervical smears is the most widely used cervical cancer screening method, but is not ideal, as the sensitivity for detection of CIN2 and higher (CIN2+) is only ~55%[3-5]. Cervical carcinogenesis is highly associated with high-risk human papillomavirus (hrHPV)[6]. Large randomized-controlled trials have shown that the sensitivity of hrHPV testing is significantly higher than cytology testing[4,7-10]. However, the specificity of hrHPV testing, especially in a young screening population is relatively low[3,11-13], which may lead to unnecessary referrals to the gynecologist, anxiety in the false-positive women, and higher costs for the health-care system. Finally, in the near future the prevalence of CIN and cervical cancer will probably decrease in countries that have introduced primary prevention with hrHPV vaccination. With this decrease in prevalence, the positive predictive value of the current screening tests will by definition decrease[14]. Therefore, other objective biomarkers with both high sensitivity as well as high specificity are needed as new screening tools for cervical cancer.

Different DNA methylation patterns in normal versus (pre)malignant lesions represent excellent targets for diagnostic approaches based on methylation specific PCR (MSP). Promoter hypermethylation of tumor suppressor genes is an early event in cervical carcinogenesis and consequently hypermethylation analysis can be especially relevant for the early detection of cervical neoplasia[15-17]. Assessment of methylation markers in cervical scrapings for the detection of CIN and cervical cancer is feasible[17-23]. See also WO2006/007980. However, finding methylation markers with both high sensitivity as well as high specificity remains a challenge.

Through the years gradually more sophisticated approaches have been developed to identify new methylation markers on a genome-wide scale[24]. Amidst comparable studies from other groups we have previously reported our experience with pharmacological unmasking of the promoter region combined with re-expression as analyzed by microarrays, high-throughput quantitative methylation specific PCR (QMSP) on an OpenArray platform and methyl-DNA immunoprecipitation followed by microarray analysis (MeDIP), resulting in the discovery and validation of the genes C13ORF18, JAM3, EPB41L3 and TERT[21,22,25]. See also WO2009/115615. The diagnostic performance of these genes showed sensitivities for detecting CIN2+ in a hrHPV positive population between 43%-71% and specificities between 89%-100%[21]. However, strategies for discovering new methylation markers so far were based on the difference between cancer and normal tissue resulting in markers with high sensitivity for carcinoma, but with too low sensitivity for detecting CIN2/3 lesions. In our MeDIP study DNA methylomes of normal and CIN3 lesions were analyzed[25]. However, a disadvantage of this technique is that it primarily recognizes bulk quantities of highly methylated repetitive DNA, resulting in less specificity.

Accordingly, the present inventors set out to identify and validate new methylation markers that can differentiate between normal cervices and CIN2/3 lesions. To that end, a novel and more specific innovative genome-wide methylation analysis of DNA from CIN2/3 lesions versus normal cervical tissue was developed. Methylated-CpG island recovery assay (MIRA) using antibody-coupled methyl-binding domain (MBD) of human MeCP2 to specifically purify methylated DNA was applied. The higher affinity of the MBD complex for double-stranded CpG-methylated DNA results in a higher enrichment for methyl DNA sequences as compared to MeDIP analysis. Next-generation-sequencing then revealed the identified novel methylated regions (MethylCap-seq). Diagnostic evaluation in cervical scrapings showed that for 8 newly identified genes the relative level of methylation increases with the severity of the underlying histological lesion. The novel methylation markers can be advantageously applied as a triage test in hrHPV positive women from population-based screening. A combination of markers was found to provide an improved diagnostic value.

In one embodiment, the invention provides a method of identifying a cervical cell as neoplastic or predisposed to neoplasia in an isolated sample, comprising determining the methylation status of at least two marker genes selected from the group consisting of KCNIP4, GATA4, GFRA1, ST6GALNAC5, CDH6, ZSCAN1, ANKRD18CP (also known in the art as AL590705.4) and LHX8.

More specifically, it was found that hypermethylation of these genes is indicative for cervical cancer. Accordingly, a method according to the invention preferably comprises determining whether said marker genes are hypermethylated, herein also referred as "methylation positive".

Some of the above markers have been individually implicated in disease. For example, WO2009/115615 discloses a set of 111 individual markers, among which GATA4, whose methylation status is linked to cervical cancer. Analysis of the methylation status of either KCNIP4, GFRA1, ST6GALNAC5, CDH6 or ZSCAN1 is reported in the art for various types of cancer. However, their prognostic value for cervical cancer was never disclosed. The prior art is completely silent about a link between the methylation status of ANKRD18CP or LHX8 and disease. Thus, the prognostic value of a marker gene combination of the present invention for identifying cervical neoplasia (CIN2/3) is not disclosed or suggested in the art.

In one embodiment, a method of the invention comprises determining the methylation status of at least KCNIP4, and/or at least GATA4, and/or at least GFRA1, and/or at least ST6GALNAC5, and/or at least CDH6, and/or at least ZSCAN1, and/or at least ANKRD18CP, and/or at least LHX8. Preferred combinations of two methylation markers include ANKRD18CP and CDH6; GFRA1 and CDH6; and GFRA1 and ANKRD18CP.

The accession numbers corresponding to the listed genes can be found at the National Center for Biotechnology Information website. Of course, as appropriate, the skilled person would appreciate that functionally relevant variants of each of the gene sequences may also be detected according to the methods of the invention. For example, the methylation status of a number of splice variants may be determined according to the methods of the invention. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences in the database entries. Computer programs for determining percentage nucleotide sequence identity are available in the art, including the Basic Local Alignment Search Tool (BLAST) available from the National Center for Biotechnology Information.

In one embodiment, the method comprises determining the methylation status of at least three, preferably at least four, more preferably at least five marker genes selected from the group consisting of KCNIP4, GATA4, GFRA1, ST6GALNAC5, CDH6, ZSCAN1, ANKRD18CP and LHX8. For example, each of the following marker gene combinations can be used:

GFRA1, ANKRD18CP and CDH6;
GFRA1, ANKRD18CP and LHX8.
GFRA1, CDH6, and LHX8.
GFRA1, CDH6, ANKRD18CP and LHX8.
GFRA1, CDH6, ZSCAN1, and ANKRD18CP.
GFRA1, CDH6, ZSCAN1, ANKRD18CP and LHX8.

In one preferred aspect, the methylation status of at least KCNIP4, ST6GALNAC5 and/or ZSCAN1 is determined. In another preferred aspect, the methylation status of at least one of CDH6, GATA4 and LHX8 is detected. In yet another preferred aspect, the methylation status of at least one of GFRA1 and ANKRD18CP, or at least one of ANKRD18CP and LHX8 is detected.

In a specific embodiment, the methylation status of KCNIP4, GATA4, GFRA1, ST6GALNAC5, CDH6, ZSCAN1, ANKRD18CP and LHX8 is determined.

It is possible for the methods of the invention to be used in order to detect more than one gene of interest in the same reaction. Through the use of several specific sets of primers, amplification of several nucleic acid targets can be performed in the same reaction mixture. This may be termed "multiplexing". Multiplexing can also be utilized in the context of detecting both the gene of interest and a reference gene in the same reaction.

As will be understood, the marker panel of the invention can be combined or supplemented with any marker gene or marker gene combination known in the art to be for useful for identifying, diagnosing, prognosing, and/or screening for cervical cancer. See for example WO2004/087957 WO2006/007980, WO2009/115615 or WO2011/036173.

Combining the newly identified genes with our previously reported panel (C13ORF18, JAM3, EPB41L3 and TERT; see WO2011/036173) surprisingly revealed that for the combinations JAM3/ANKRD18CP, C13ORF18/JAM3/ANKRD18CP and JAM3/GFRA1/ANKRD18CP sensitivities for CIN2+ are between 72-74%, which is comparable to the sensitivity for CIN2+ of hrHPV testing (79%). Specificities of our gene panel was between 76-79%, which is significantly higher (p≤0.05) than the specificity for hrHPV testing (42%) in a triage setting after a positive Pap smear test result in population-based screening.

Accordingly, in one embodiment, the panel of marker genes further comprises at least one of JAM3, EPB41L3 and C13ORF18. For example, it comprises determining the methylation status of the genes of at least one of the following panels of marker genes:

ANKRD18CP, CDH6 and EPB41L3
GFRA1, EPB41L3 and CDH6;
GFRA1, ANKRD18CP and CDH6;
GFRA1, EPB41L3 and ANKRD18CP;
JAM3, GFRA1 and ANKRD18CP.

Also provided herein is a method of identifying a cervical cell as neoplastic or predisposed to neoplasia in an isolated sample, comprising determining the methylation status of a panel of at least a first and second marker genes, wherein the at least first marker gene is selected from the group consisting of KCNIP4, GFRA1, ST6GALNAC5, CDH6, ZSCAN1, ANKRD18CP and LHX8, and wherein the at least second marker gene is selected from JAM3, EPB41L3 and C13ORF18. Preferably, the marker gene panel comprises at least one of the following combinations of marker genes:

JAM3/CDH6; ANKRD18CP/CDH6/EPB41L3; GFRA1/EPB41L3/CDH6; CDH6/EPB41L3; JAM3/EPB41L3/ANKRD18CP; C13ORF18/JAM3/ANKRD18CP; GFRA1/EPB41L3/ANKRD18CP; ANKRD18CP/EPB41L3; C13ORF18/CDH6; JAM3/GFRA1/ANKRD18CP; C13ORF18/JAM3/EPB41L3; JAM3/ANKRD18CP; JAM3/EPB41L3/GFRA1; GFRA1/EPB41L3; C13ORF18/JAM3/GFRA1; JAM3/GFRA1 and C13ORF18/ANKRD18CP.

As shown herein below, a method according to the invention allows detection of CIN2 or higher (CIN2+) cervical cancer with increased sensitivity and/or increased specificity over existing methods. In one embodiment, it allows detection of CIN2+ cervical cancer with a sensitivity and/or a specificity of at least 65%, preferably at least 70%. For example, both sensitivity and specificity are at least 66%, 67%, 68%, 69%, 70%, 71%, 72%, 73%, 74% or 75%.

The sample to be analyzed can be a cervical scraping, preferably a self-collected vaginal swab, or wherein the sample is a liquid based cytology sample.

The advantage of methylation analysis is that is an objective test and that it can be performed on the same material used for hrHPV testing, which makes it also interesting for self-sampled material. Different methylation markers already have been tested as a triage test in hrHPV positive women. However, for most markers a cut-off value was set in order to obtain high specificity. The advantage of the newly found markers is that no cut-off value is needed. If the PCR product is negative (i.e. no amplification of specific product), the samples are called negative and any ratio above zero is called positive. This unique feature of the selected genes allows an objective and easy to interpret test.

Methods to determine the methylation status of the marker genes are known in the art. In one embodiment, at least one pair of oligonucleotide primers is designed not to contain cytosines and amplifies modified and unmodified sequences. An additional amplification may be subsequently performed with primers hybridizing to the modified sequence, thereby indicating methylation; or alternatively a detection step with a specific probe may be performed, thereby indicating methylation. Alternatively, the amplification may be combined with restriction cutting by using methylation sensitive enzymes; only the methylated region is amplified in this case.

Alternatively, methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Alternatively, chemical reagents can be used that selectively modify either the methylated or non-methylated form of CpG dinucleotide motifs, thereby transforming the CpG-dinucleotide motifs. Modified products can be detected directly, or after a further reaction which creates products that are easily distinguishable. Means which detect altered size and charge can be used to detect modified products, including but not limited to electrophoresis, chromatography, and mass spectrometry. Examples of such chemical reagents for selective modification include hydrazine and bisulfite ions. Hydrazine-modified DNA can be treated with piperidine to cleave it.

Bisulfite ion-treated DNA can be treated with alkali. In one embodiment of the present invention, methylation is detected by contacting at least a portion of the applicable gene or promoter region thereof with a chemical reagent that selectively modifies a non-methylated cytosine residue relative to a methylated cytosine residue, or selectively modifies a methylated cytosine residue relative to a non-methylated cytosine residue; and detecting a product generated due to said contacting. In a further embodiment, the chemical reagent comprises bisulfite ions. In a further embodiment, the method further comprises treating with alkali the bisulfite ion-contacted portion of the gene.

Other means for detection that are reliant on specific sequences can be used, including but not limited to electrophoresis, hybridization, amplification, quantitative methylation-specific PCR (QMSP), sequencing, ligase chain reaction, chromatography, mass spectrometry. Combinations of such techniques may also be used.

In a preferred embodiment, a method of the invention involves determining the methylation status of the genes using methylation specific PCR (MSP), preferably real-time quantitative methylation specific PCR (QMSP). To adjust for DNA input, hypermethylation ratios are advantageously calculated against DNA levels of a reference gene, for instance beta-actin or beta-catenin.

In a specific aspect, the methylation status is determined using a set of primers comprising or consisting of a sequence selected from entries 1-16 of Table 1A and/or a probe comprising or consisting of a sequence selected from entries 17-24 of Table 1B.

In a related embodiment, the invention provides for a method for cervical cancer detection or screening comprising the steps of: a) performing cytology evaluation on a test sample comprising cervical cells or nucleic acids from cervical cells; b) if a) is positive, assaying the methylation status of at least two genes selected from the group consisting of KCNIP4, GATA4, GFRA1, ST6GALNAC5, CDH6, ZSCAN1, ANKRD18CP and LHX8; c) if the at least two genes of b) are methylated, refer the woman for colposcopy; d) if the at least two genes of b) are unmethylated, refer the woman to cytology testing on a more regular basis.

In a related embodiment, the invention provides for a method for cervical cancer detection or screening comprising the steps of: a) assaying the methylation status of at least two genes selected from the group consisting of KCNIP4, GATA4, GFRA1, ST6GALNAC5, CDH6, ZSCAN1, ANKRD18CP and LHX8; b) if the at least two genes of a) are methylated, perform cytology testing; c) if b) is tested positive, refer the woman for colposcopy; d) if b) is negative, refer the woman to follow-up after 6 month for HPV-testing.

The invention also relates to a kit for use in identifying a cervical cell as neoplastic or predisposed to neoplasia, preferably cervical neoplasia (CIN2/3), in an isolated sample. A kit of the invention is characterized by the presence of gene specific primers for at least two genes selected from the group consisting of KCNIP4, GATA4, GFRA1, ST6GALNAC5, CDH6, ZSCAN1, ANKRD18CP and LHX8; gene specific probes for said at least two genes; and preferably a tool for removing cervical cells from a subject, such as an Ayre's spatula and/or an endocervical brush.

In another embodiment, the kit comprises gene specific primers for of at least two marker genes, wherein the at least first marker gene is selected from the group consisting of KCNIP4, GFRA1, ST6GALNAC5, CDH6, ZSCAN1, ANKRD18CP and LHX8, and wherein the at least second marker gene is selected from JAM3, EPB41L3 and C13ORF18; gene specific probes for said at least two genes; and optionally an Ayre's spatula and/or an endocervical brush for removing cervical cells from a subject.

Preferably, the kit comprises gene specific primers for at least one of the following combinations of marker genes:

JAM3/CDH6; ANKRD18CP/CDH6/EPB41L3; GFRA1/EPB41L3/CDH6; CDH6/EPB41L3; JAM3/EPB41L3/ANKRD18CP; C13ORF18/JAM3/ANKRD18CP; GFRA1/EPB41L3/ANKRD18CP; ANKRD18CP/EPB41L3; C13ORF18/CDH6; JAM3/GFRA1/ANKRD18CP; GFRA1/CDH6; JAM3/ANKRD18CP; JAM3/EPB41L3/GFRA1; GFRA1/EPB41L3; C13ORF18/JAM3/GFRA1; JAM3/GFRA1; and C13ORF18/ANKRD18CP.

Preferred primers and probes for use in a kit of the invention are selected from the primers and probes comprising or consisting essentially of the nucleotide sequences set forth in Table 1A or 1B. In one embodiment, the kit comprises one or more gene specific primer(s) comprising or consisting of a sequence selected from entries 1-16 of Table 1A. Alternatively or additionally, the kit comprises at least one gene specific probe comprising or consisting of a sequence selected from entries 17-24 of Table 1B.

Related to this, the invention also provides for an isolated polynucleotide which consists of a nucleotide sequence listed in Table 1A or Table 1B.

The kit may additionally comprising gene specific reagents for further gene(s) whose methylation status is linked to the incidence of cervical cancer, preferably wherein said further gene(s) comprises JAM3, EPB41L3 and/or C13ORF18.

LEGENDS TO THE FIGURES

FIG. 1: Flow scheme of the strategy used for the identification of new CIN2+ methylation markers.

Figure 2:
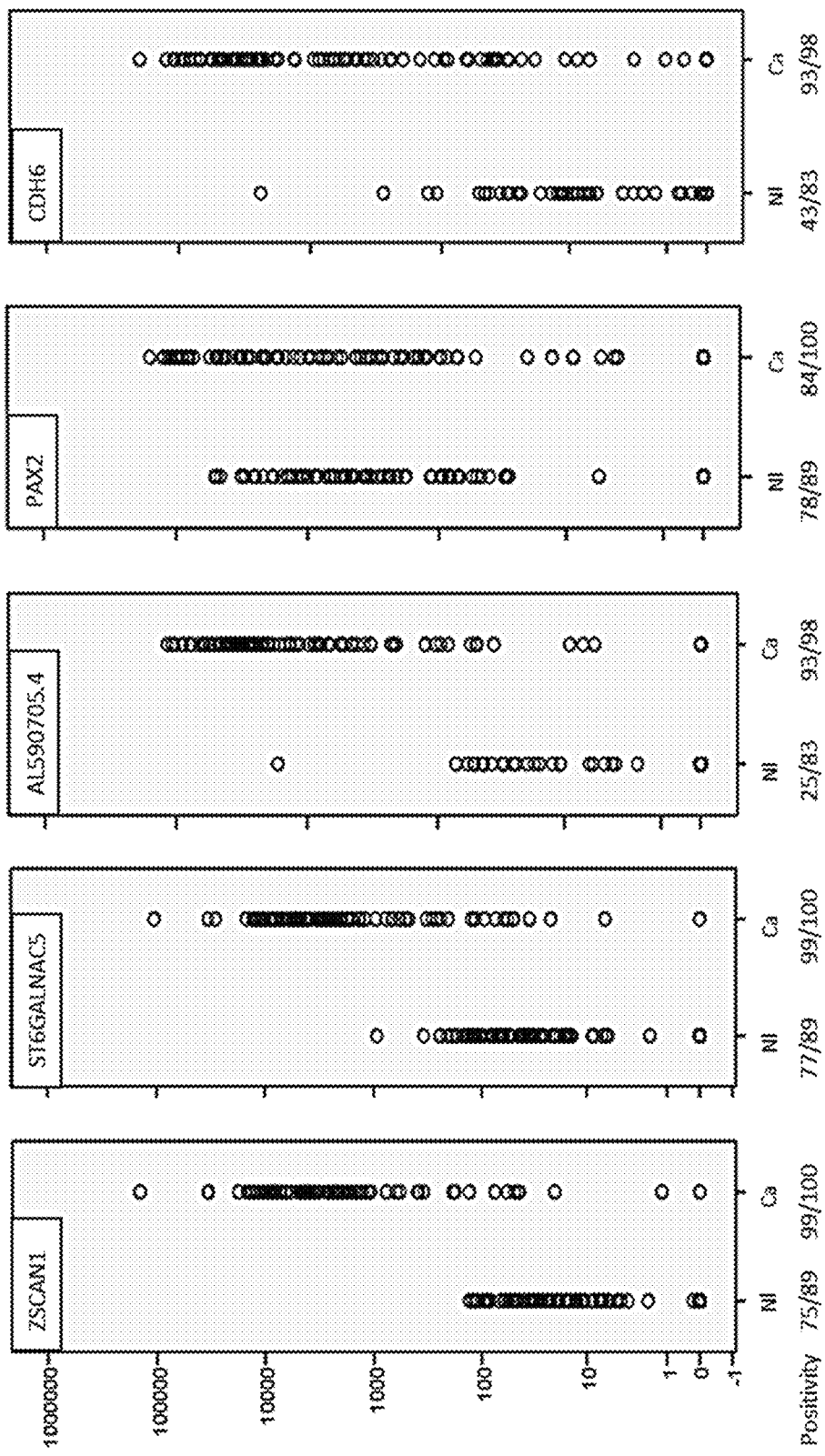
Figure 2:
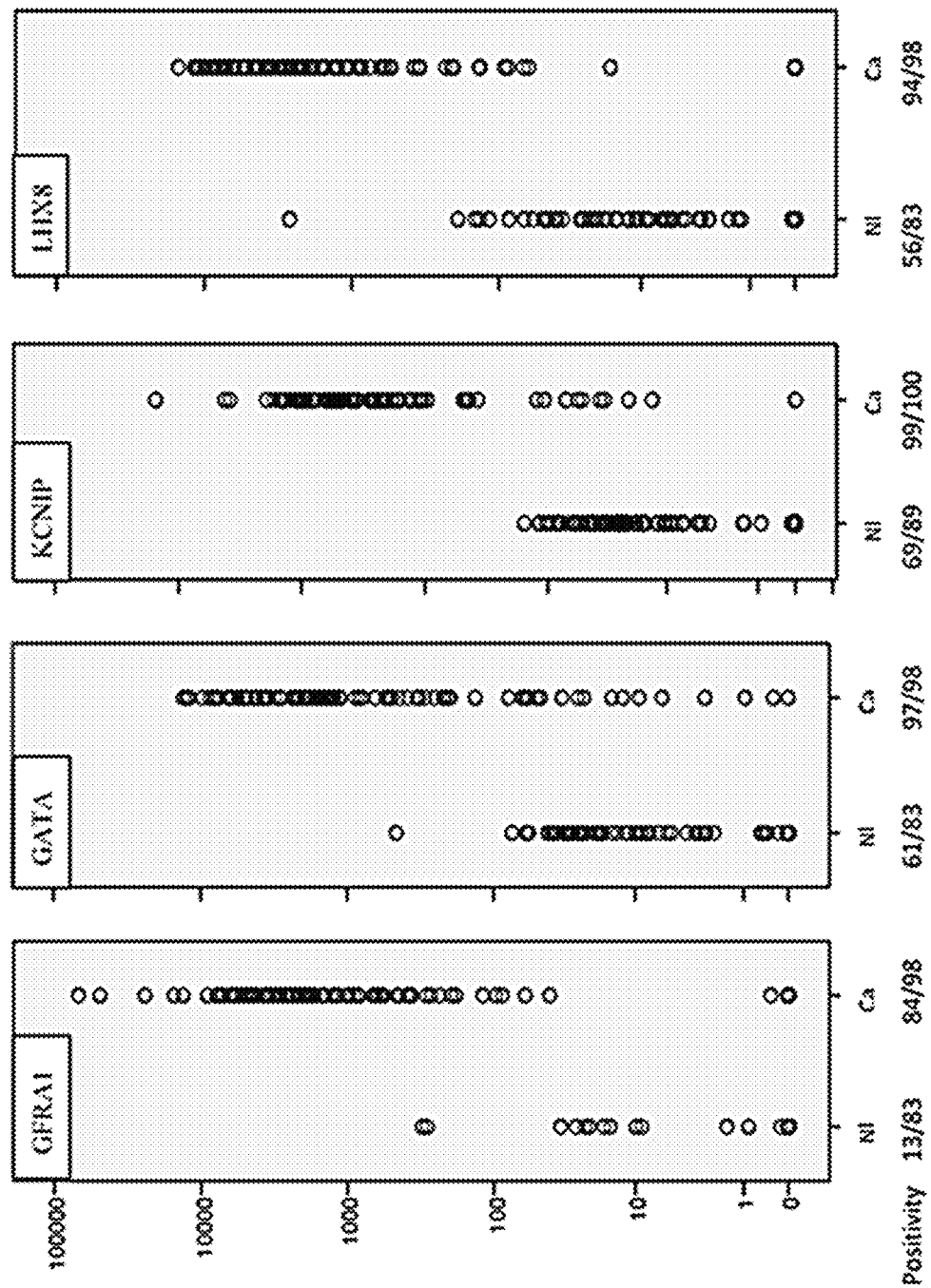

FIG. 2: Methylation ratio of 9 genes tested with QMSP in scrapings from normal (Nl) and cancer (Ca) patients. Relative levels of methylation is significantly higher in the cancer scrapings (all genes, except PAX2, $p<0.001$).

Figure 3:
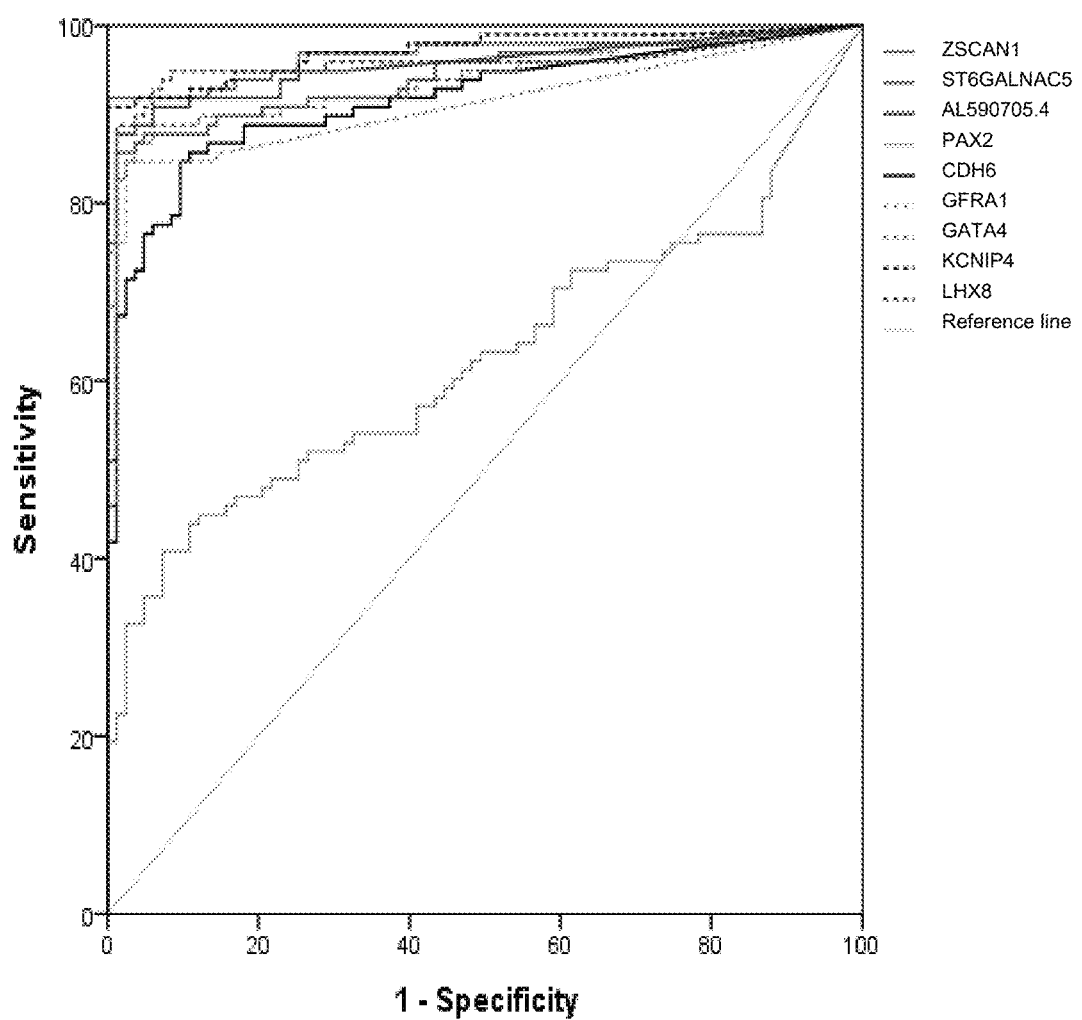

FIG. 3: ROC curve analyses of methylation ratio's per gene.

Figure 4:
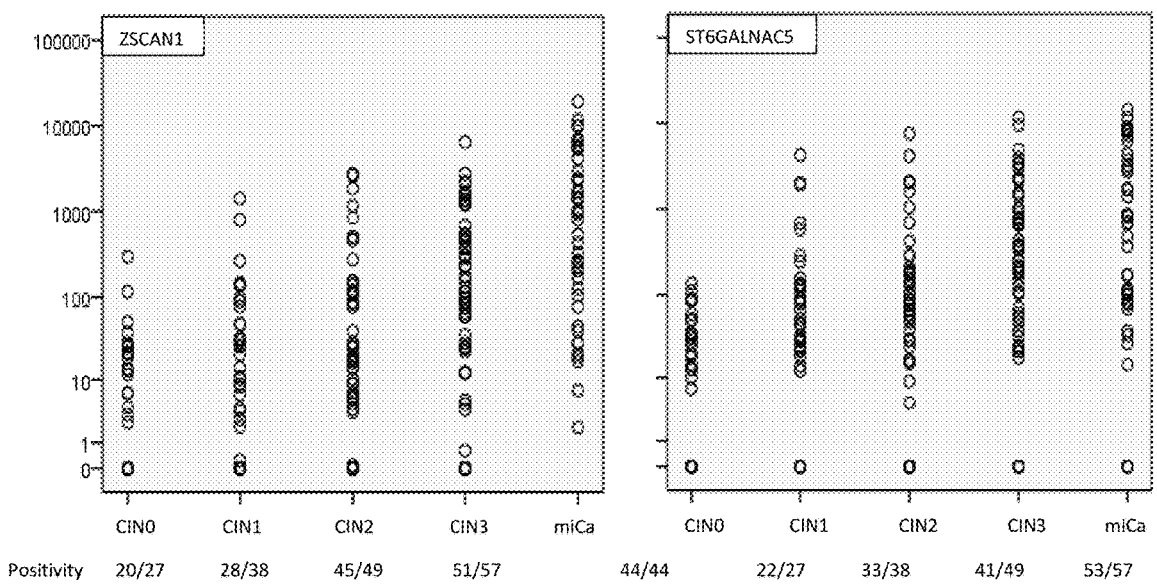
Figure 4:
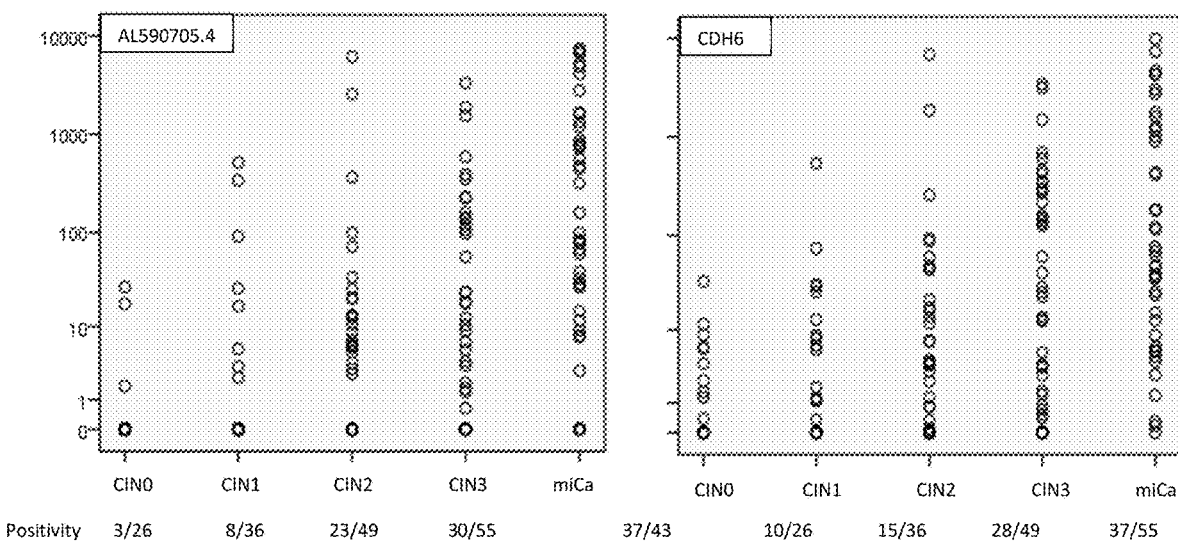
Figure 4:
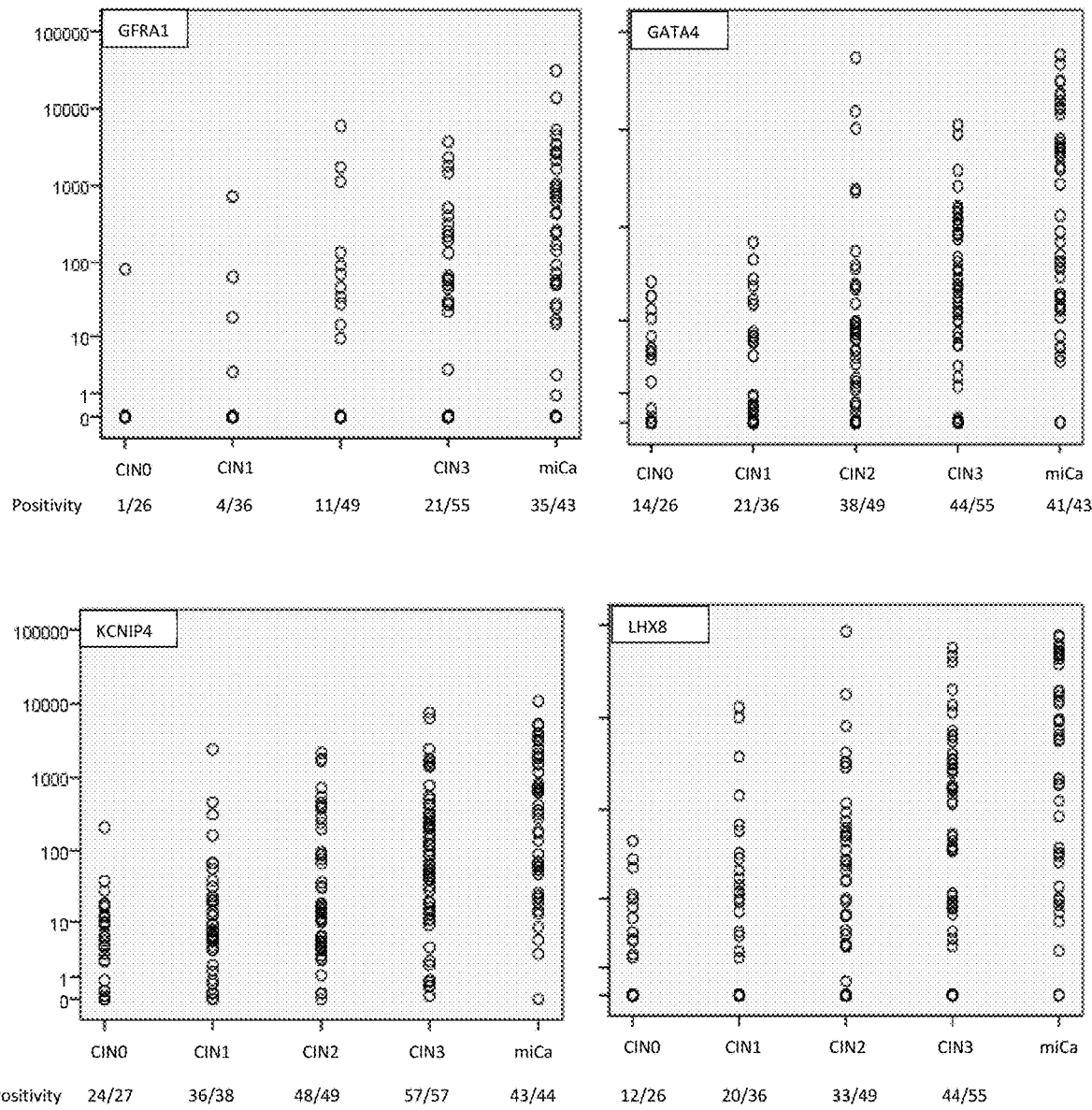

FIG. 4: Methylation ratio of each of 8 novel marker genes tested with QMSP in scrapings from patients with CIN0, CIN1, CIN2, CIN3 and (mi)Ca. Relative levels of methylation significantly increase with more severe histological abnormality (all $p<0.001$).

EXPERIMENTAL SECTION

Patients and Methods

General Strategy

To characterize the DNA methylome of CIN2/3 lesions and to identify new CIN2 or higher (CIN2+) methylation markers, we applied the following strategy (see FIG. 1): First, methylated DNA was enriched using MBD of human MECP2 with subsequent paired-end sequencing (Methyl-Cap-seq) on DNA isolated from fresh-frozen macro-dissected epithelial tissue of 18 CIN2/3 lesions (6 CIN2 and 12 CIN3), 20 normal cervices and two pools of leukocyte DNA of healthy volunteers. In order to identify differential methylated regions (DMRs), we retrieved the reads of promoter and exon regions. We selected methylation markers that showed significant differences between the normal and CIN2/3 cervices, while also the leukocyte count had to be low, to prevent false-positive results. Markers were ranked on high specificity (no methylation in the normal cervices) and high sensitivity (methylation in CIN2/3 lesions). For the highest ranking top15 genes, methylation specific PCR (MSP) primers were designed and methylation patterns were verified on the same DNA, which originally was used for MethylCap-seq. This first validation step enabled verification of MethylCap-seq data by correlating MSP band intensity with the number of reads from the MethylCap-seq. In the second validation step high prevalence of methylation in the CIN2/3 lesions and no methylation in the normal cervices was analyzed by MSP analysis on DNA isolated from a completely independent cohort of patients (cervical cancer (n=13), CIN2/3 lesions (n=19) and normal cervices (n=17)). DNA was isolated from macro-dissected formalin fixed paraffin embedded (FFPE) epithelial tissue.

Finally, diagnostic evaluation of the newly discovered methylation markers was performed by QMSP on cervical scrapings. First, we tested the methylation ratios of new biomarkers on a large series of randomly selected scrapings from cervical cancer patients (n=100) and a similar age group of healthy controls (n=89). Secondly, the potential of the new methylation markers as a diagnostic tool was evaluated in a large series of scrapings (n=215) of randomly selected patients, referred with an abnormal Pap smear at population-based screening. Histology was used as the reference standard.

Patient Samples

All patients referred to the outpatient clinic of the University Medical Center Groningen (UMCG) with cervical cancer or an abnormal Pap smear at population-based screening are routinely asked to participate in our ongoing 'Methylation study' which has been approved by the Institutional Review Board (IRB) of the UMCG. Cervical tissue, scrapings and clinicopathologic data are prospectively collected and stored in our tissue bank. Within our Methylation study tissue samples, scrapings and clinicopathologic data from normal cervices are also collected from patients planned to undergo a hysterectomy for non-malignant reasons. All cervical tissue that was used for the normal control group was judged as histopathological normal. Patients referred with cervical cancer are staged according to the FIGO criteria with pelvic examination and biopsies under general anaesthesia. Cervical scrapings from both groups (cervical cancer staging and benign gynecologic surgery) were collected before surgery under general anaesthesia. All patients referred with an abnormal Pap smear at population-based screening underwent an additional Pap smear prior to colposcopy specifically for this study. At colposcopy, biopsies and/or Large Loop Excision of the Transformation Zone (LLETZ) were performed. The tissue samples were scored by an experienced gynaecologic pathologist and the histological classification was used as the reference standard. If no interference with routine diagnostic evaluation was anticipated, specimens from the CIN lesions were retrieved and stored at −80° C. Clinicopathological data were retrieved from patient files and stored in our large anonymous password-protected institutional Gynecologic Oncology database. All patients gave written informed consent.

For the frozen tissue samples used in de MethylCap-seq analysis, the median age of the CIN2/3 patients was 35 years (IQR 30-39) and for the patients with normal cervices 43 years (IQR 41-44). For the independent cohort of patients with FFPE samples, the median age of the CIN2/3 patients was 37 years (IQR 34-41), for the patients with normal cervices 43 years (IQR 40-44) and for the cervical cancer patients 49 years (range 42-54). For the cervical scrapings the median age of cervical cancer patients was 50 years (IQR 39-64) and for the patients with normal cervices 47 years (IQR 43-53). The stage of cervical cancer patients was: 1 (1%) FIGO stage IA1, 31 (31%) FIGO stage IB1, 18 (18%) FIGO stage IB2, 21 (21%) FIGO stage IIA, 17 (17%) FIGO stage IIB, 1 (1%) FIGO stage IIIA, 8 (8%) FIGO stage IIIB and 3 (3%) FIGO stage IV. Histological classification of the cervical cancer patients was: 70 (70%) squamous cell carcinoma (SCC), 21 (21%) adenocarcinoma (AD), 3 (3%) adenosquamous (ASC) and 6 (6%) undifferentiated carcinoma. The median age of the patients referred with an abnormal Pap smear was 37 years (IQR 32-43). The histological classifications of these patients were: 27 without CIN, 38 CIN1, 45 CIN2, 61 CIN3 and 44 miCa (29 SCC, 12 AD, 3 ASC). The Pap smears were classified according to the Papanicolaou system. Table 4 shows per histological subgroup, the Pap classification (and translation to Bethesda).

From all frozen tissue samples used for MethylCap-seq and the FFPE samples, 10 µm tissue sections were cut and macrodissection was performed to enrich for epithelial cells. Before and after cutting a hematoxylin and eosin slide was made to check presence of epithelial cells. Cervical scrapings were collected in 5 ml ice-cold phosphate buffered saline (PBS: 6.4 mM $NA_2HPO_4$; 1.5 mM $KH_2PO_4$; 0.14 M NaCl; 2.7 mM KCl) and kept on ice until further processing. Of these 5 ml cell suspension, 1 ml was used for cytomorphological assessment. The remaining 4 ml was centrifuged and the cell pellet was suspended in 1 ml TRAP wash buffer and divided in 4 fractions. Two fractions were stored as dry pellet at −80° C. for DNA isolation as described previously[21].

DNA Isolation

Tissue slides from FFPE tissue were deparaffinized using 100% xylene followed by 100% ethanol[17]. Genomic DNA from fresh-frozen macro-dissected samples and cervical scrapings was isolated by standard overnight 1% SDS and Proteinase K treatment, salt-chloroform extraction and isopropanol precipitation as described previously[21]. DNA pellets were washed with 70% ethanol and dissolved in 150 µl TE[−4] (10 mM Tris/HCL; 0.1 mM EDTA, pH 8.0). Genomic DNA was amplified in a multiplex PCR according to the BIOMED-2 protocol, to check the DNA's structural integrity[27]. For the MethylCap-seq samples, DNA quantity was measured using Quant-iT™ PicoGreen® dsDNA Assay Kit according to manufacturer's protocol (Invitrogen, Carlsbad, Calif., USA). For cervical scrapings DNA concentrations and 260/280 ratios were measured using the Nanodrop ND-1000 Spectrophotometer (Thermo Scientific, Waltham, Mass., USA). A 260/280 ratio of >1.8 was required for all samples.

Methylated-CpG Island DNA Capturing Followed by Next-Generation Sequencing (MethylCap-seq)

Methylated DNA fragments were captured with methyl-binding domains using the MethylCap kit according to manufacturers instructions (Diagenode, Liège, Belgium). The kit consists of the methyl binding domain (MBD) of human MeCP2, as a C-terminal fusion with Glutathione-S-transferase (GST) containing an N-terminal His6-tag. Before capturing, DNA samples (500 ng) were sheared to a size range of 300-1000 bps using a Bioruptor™ UCD-200 (Diagenode, Liège, Belgium) and fragments of ~300 bp were isolated. Leukocyte DNA of 4 healthy controls were included in 2 sets of 2 samples. Captured DNA was paired-end-sequenced on the Illumina Genome Analyzer II platform according to protocol (Illumina, San Diego, Calif., USA). Results were mapped on the nucleotide sequence using Bowtie software[28], visualized using BioBix' H2G2 browser and processed using the human reference genome (NCBI build 37). The paired-end fragments were unique and located within 400 bp of each other[29].

MethylCap-Sequencing Analysis

For statistical analysis, reads of promoter (−2000 bp-to +500 bp of transcription start site) and exon regions were retrieved. In order to identify differences between normal cervices and CIN2/3 lesions, we dichotomised the read data into methylation positive or negative. Samples were considered negative if a sample showed either 0 or 1 read. Samples were considered methylation positive if a sample showed ≥3 reads. Subsequently, regions were ranked based on highest specificity and highest sensitivity for CIN2/3. The candidate markers should fulfil the following criteria: 1) Low/negative reads in the leukocytes to prevent false positive results. The region was excluded if both leukocyte samples showed >1 read or if 1 leukocyte sample showed >2 reads. 2) Unmethylated (0 or 1 read) in at least 75% (15/20) of the normal cervix group. 3) Methylated (>3 reads) in at least 28% (5/18) of the CIN2/3 lesion group.

Verification and Validation of MethylCap-Sequencing Data by Methylation Specific PCR (MSP)

MSP primers were designed for the highest ranking top 15 genes (16 DMRs). Sodium bisulfite treatment of isolated genomic DNA (1 μg/sample) was performed according to the recommendations of the EZ DNA methylation kit (Zymo, BaseClear, Leiden, the Netherlands). MSP design and analysis was performed using sequences derived from the H2G2 browser. Each reaction was performed in 30 μl total reaction volume, containing: 600 nM of each MSP primer, 1.5 μl of bisulphite treated DNA (approximately 15 ng), standard PCR components (Applied Biosystems) and 0.5 U AmpliTaq Gold DNA polymerase (Applied Biosystems). Condition of the MSP was: 10 min hot-start at 95° C.; 95° C. for 60 sec, 60° C. for 60 sec, 72° C. 60 sec for a total of 40 cycles, with a final elongation step of 7 min at 72° C. Leukocyte DNA from healthy women was used as negative control and in vitro methylated (by SssI enzyme) leukocyte DNA was used as positive control for each MSP.

Quantitative Methylation Specific PCR (QMSP)

QMSP was performed as described previously by our group with an internal (FAM-ZEN/IBFQ)-labelled hybridisation probe for quantitative analyses[21]. Primer and probe sequences are summarized in Table 1. β-actin was used as a methylation independent internal reference gene.

TABLE 1A

Primer and probe sequences used in Quantitative Methylation Specific PCR (QMSP)

| Gene | Forward primer 5'→3' | Reverse primer 5'→3' |
| --- | --- | --- |
| ZSCAN1 | TTGTTGGTAT-TCGTTTGTTC (SEQ ID NO: 1) | ACGCGACCGAACGATATT (SEQ ID NO: 2) |
| ST6GALNAC5 | GTAGTTGCGGATG-GAGGTTC (SEQ ID NO: 3) | CTAACTACGCTCACCCTCCG (SEQ ID NO: 4) |
| ANKRD18CP | CGATGTGGTATTTTC-GATTC (SEQ ID NO: 5) | ACGTCTAAAAAATCGCCAC (SEQ ID NO: 6) |
| CDH6 | GGGCGGCGTTGTTGTC (SEQ ID NO: 7) | CCAACCCCACGACGAATC (SEQ ID NO: 8) |
| GFRA1 | TAGGGGGAATCGATGTTTC (SEQ ID NO: 9) | GAATCCTAAACACCGAACGA (SEQ ID NO: 10) |

TABLE 1A-continued

Primer and probe sequences used in Quantitative Methylation Specific PCR (QMSP)

| Gene | Forward primer 5'→3' | Reverse primer 5'→3' |
| --- | --- | --- |
| GATA4 | GGTCGGGTTAATTCGGTC (SEQ ID NO: 11) | CCTCGACAAAACTCAAAACG (SEQ ID NO: 12) |
| KCNIP4 | GGGACGTAGGGTGTAGAAGCAAACTCTCGCTCCCAACG (SEQ ID NO: 13) | (SEQ ID NO: 14) |
| LHX8 | TATTTTTTTCGTAGCG-GATC (SEQ ID NO: 15) | ACGAAAAACCAAATTCTACG (SEQ ID NO: 16) |

TABLE 1B

Probe sequences used in Quantitative Methylation Specific PCR (QMSP)

| Gene | 6FAM/ZEN/IBFQ probe 5'→3' |
| --- | --- |
| ZSCAN1 | AGGTCGAAGTTTTTTTACGTATTTTTATTGTTCGT TTA (SEQ ID NO: 17) |
| ST6GALNAC5 | TTGAAGTTTCGGGTTTGGTCGTCGAGTC (SEQ ID NO: 18) |
| ANKRD18CP | AGGAGCGTTTGGTTTAGGCGTTTTTCG (SEQ ID NO: 19) |
| CDH6 | CGTTTTTCGGGGAGTTTGGGTATCGTTTTTTCG (SEQ ID NO: 20) |
| GFRA1 | TTTATTCGTCGCGCGTTTTCGG (SEQ ID NO: 21) |
| GATA4 | ATTTCGGTGAGTAGGAGCGCGAG (SEQ ID NO: 22) |
| KCNIP4 | TCGGTTAGGGGCGTTTGTTTACGGGTTTGTACGG (SEQ ID NO: 23) |
| LHX8 | ATTGGCGTTTTGCGAATCGG (SEQ ID NO: 24) |

QMSP reactions were performed in 10 μl final volume, containing: 300 nM of forward and reverse primers, 250 nM of hybridisation probe, 5 μl of 2*QuantiTech Probe PCR Master Mix (Qiagen Hilden, Germany) and 2.5 μl bisulfite modified DNA (approximately 25 ng). Each sample was analyzed in triplicate by ABI PRISM® 7900HT Sequence Detection System (Applied Biosystems). Negative and positive controls were the same as used for MSP. Standard curve analysis was performed on each plate and by each primers-probe set on serial dilutions of in vitro methylated leukocyte DNA. A DNA sample was considered methylated if at least 2 out of the 3 wells were methylation positive with a Ct-value below 50 and DNA input of at least 225 pg β-actin. The relative level of methylation of the region of interest was determined by the following calculation: the average quantity of the methylated region of interest divided by the average quantity of the reference β-Actin gene and multiplied by 10000[30]. In our analysis we also included 4 genes previously described by our group (C13ORF18, JAM3, EPB41L3 and TERT) to compare sensitivity and specificity of these known genes with the newly identified methylation markers. QMSP for these markers was performed as previously described[21].

HPV Testing

HrHPV testing was performed using general primer-mediated PCR (GP5+/6+) as reported previously[30]. For HPV-typing as well as detection of the clinical relevant HPV infections, GP5+/6+ positive cases were tested by COBAS® 4800 HPV test. The COBAS HPV test individually detects HPV 16 and 18, while at the same time identifying 12 additional hrHPV types[31]. The COBAS HPV test is routinely used in our iso-15189-certified laboratory of molecular pathology on scrapings from the national population-based screening program. For the COBAS® HPV testing in this study, the PCR only workflow was used, since no liquid-based scrapings in Preservcyt® were available but only already isolated DNA. This workflow was first validated with DNA isolated from clinical samples that were tested previously in the diagnostic routine and this showed comparable results to the liquid-based samples.

Statistical Analysis

Statistical analysis was performed using SPSS software package (SPSS 20, Chicago, Ill., USA). Spearman's rank correlation coefficient was used to compare the MethylCap-seq reads with the MSP band intensity. Categorical methylation data were analyzed using the Pearson $\chi^2$ test. Receiver operating characteristic (ROC) curves were generated and the area under the ROC curve (AUC) was used as a measure of test performance. The Mann-Whitney U test and Kruskall-Wallis test was used to determine differences in methylation ratio in 2 groups or more, respectively. The student T test was used to compare positive methylation and age. To compare sensitivity and specificity of the patient group referred with abnormal cytology by DNA methylation markers versus hrHPV, the extended McNemar test, described by Hawass was executed[32]. P-values lower than 0.05 were considered statistically significant.

Results

Identification of Differential Methylated Genes by MethylCap Sequencing

Genome-wide MethylCap-seq was used to compare the DNA methylation profiles of CIN2/3 dysplastic cervical cells with normal cervical cells to identify CIN2/3 specific DMRs. After applying our criteria, 176 DMRs comprising 163 genes remained (data not shown).

Verification and Validation of the Top 15 Differentially Methylated Genes

To verify the MethylCap-seq data, the top 15, out of the 163 identified genes were selected. MSP primers were designed and could be optimized for 14 out of the 15 genes. Verification of the selected 14 genes showed for 11 genes a significant correlation between the MSP band intensity and the amount of reads from the MethylCap-seq data. One gene (PCDH17) showed high methylation levels in leukocytes and was therefore excluded for further validation. The remaining 10 genes passed verification and continued to the subsequent validation step. Table 2 shows an overview of which genes continued through the different stages of validation.

TABLE 2

Verification, validation and diagnostic evaluation of the highest ranking top 15 genes.

| Rank | Gene | Optimized | Verification | Validation | 1st diagnostic evaluation | 2nd diagnostic evaluation |
|---|---|---|---|---|---|---|
| 1 | ZSCAN1 | Yes | Yes | Yes | Yes | Yes |
| 2 | PCDH17 | Yes | No* | | | |
| 3 | ST6GALNAC5 | Yes | Yes | Yes | Yes | Yes |
| 4 | CLIC6 | Yes | No | | | |
| 5 | AC01234.1 | Yes | No | | | |
| 6 | ANKRD18CP | Yes | Yes | Yes | Yes | Yes |
| 7 | PAX2** | Yes | Yes | Yes | No | |
| 8 | CDH6 | Yes | Yes | Yes | Yes | Yes |
| 9 | GFRA1 | Yes | Yes | Yes | Yes | Yes |
| 10 | IRX1 | Yes | No | | | |
| 11 | POU4F3 | Yes | Yes | No* | | |
| 12 | GATA4 | Yes | Yes | Yes | Yes | Yes |
| 13 | MKX | No | | | | |
| 14 | PAX2** | Yes | No | | | |
| 15 | KCNIP4 | Yes | Yes | Yes | Yes | Yes |
| 16 | LHX8 | Yes | Yes | Yes | Yes | Yes |

*Excluded due to high methylation in leukocytes
**Same gene, different region

The second validation step was performed by MSP on DNA from FFPE tissue of an independent, randomly selected new patient cohort that consisted of 13 cervical cancers, 19 HSIL lesions (8 CIN2, 8 CIN3 and 3 adCIS) and 17 normal cervices. Out of the 10 genes analyzed, 9 showed low methylation levels in the normal samples, significant differential methylation between normal versus HSIL lesions and again little to no methylation in the leukocytes (p<0.05) (Table 3). These 9 genes (ZSCAN1, ST6GALNAC5, ANKRD18CP, PAX2, CDH6, GFRA1, GATA4, KCNIP4 and LHX8) were selected for further diagnostic evaluation in cervical scrapings (Table 3).

TABLE 3

Methylation positivity in an external cohort of FFPE samples to validate results of high methylation in CIN2+ lesions and no methylation in normal cervices of the newly found methylation markers.

| Gene | Normal | CIN2 | CIN3 | adCIS | carcinoma |
|---|---|---|---|---|---|
| ZSCAN1 | 4/16 | 8/8 | 7/8 | 3/3 | 12/13 |
| ST6GALNAC5 | 0/16 | 1/6 | 4/8 | 2/3 | 9/12 |
| ANKRD18CP | 0/16 | 1/8 | 1/7 | 2/3 | 6/12 |
| PAX2 | 1/14 | 6/8 | 7/8 | 3/3 | 5/13 |
| CDH6 | 1/15 | 3/8 | 4/8 | 3/3 | 7/13 |
| GFRA1 | 0/12 | 2/8 | 3/8 | 2/3 | 10/12 |
| POU4F3* | 2/14 | 6/7 | 3/7 | 3/3 | 11/12 |
| GATA4 | 0/17 | 3/8 | 2/7 | 3/3 | 10/13 |
| KCNIP4 | 0/17 | 6/8 | 5/8 | 3/3 | 10/12 |
| LHX8 | 1/16 | 3/8 | 4/8 | 3/3 | 7/13 |

*Excluded due to high methylation in leukocytes

Diagnostic Evaluation by QMSP for Normal Versus Cancer Scrapings

To evaluate the diagnostic value of the new methylation markers, cervical scrapings from two cohorts of patients were used: 1) normal versus carcinoma scrapings and 2) scrapings from patients referred from population-based screening with an abnormal Pap smear (≥Pap2). In cohort 1, scrapings of 100 randomly selected cervical carcinoma patients and 89 patients with histologically confirmed normal cervices were used. QMSP analysis showed that the relative levels of DNA methylation were higher in the carcinoma scrapings compared to the normal scrapings for 8 out of the 9 selected genes (p<0.001) (FIG. 2). The area under the curve (AUC) for methylation ratio in cervical carcinoma showed for 8 genes an AUC>0.91, and for one gene (PAX2) an AUC of 0.59. Therefore PAX2 was excluded from further analysis (FIG. 3). In women with a normal cervix, methylation positivity for all 9 genes was not related to age (data not shown).

Diagnostic Evaluation by QMSP for Normal/LSIL Versus HSIL Scrapings

In cohort 2, scrapings of 215 consecutive patients referred from population-based screening with an abnormal Pap smear were used. The 8 genes that showed differential methylation in the normal versus the cancer scrapings were subsequently tested in cohort 2. Methylation levels and frequencies for all 8 genes analyzed (ZSCAN1, ST6GALNAC5, ANKRD18CP, CDH6, GFRA1, GATA4, KCNIP4 and LHX8), increased with the severity of the underlying histological lesion (p<0.001) (FIG. 4 and Table 4).

Without setting a cut-off value for achieving higher/lower sensitivity and/or specificity, genes ZSCAN1, ST6GALNAC5 and KCNIP4 reached high sensitivity (≥90%) for detection of CIN2+ lesions, while for CDH6, GATA4 and LHX8 sensitivity for CIN2+ was between 73-84% (Table 5a). For ANKRD18CP and GFRA1 sensitivity for CIN2+ was between 46-61%, and these genes showed especially high specificity (82%-92%). In our analysis, we also included a marker panel of 4 genes, previously described by our group (C13ORF18, JAM3, EPB41L3 and TERT) to compare sensitivity and specificity of these known genes with the newly identified methylation markers. The gene C13ORF18 showed reproducible results as described previously[21] with high specificity (95%) and relatively low sensitivity for CIN2+ of 40%. JAM3 and EPB41L3 showed sensitivities for CIN2+ between 63-69% and specificities between 79-91%. The gene TERT was previously described with high specificity, but this result could not be reproduced since specificity was only 46% in our analysis, while sensitivity for CIN2+ lesions was 82%.

hrHPV Status and Triage Testing

HrHPV testing was performed on the patients group referred with abnormal cytology at population-based screening. For 6 out of 215 patients insufficient material was available to perform HPV testing. HrHPV was detected in 152/209 (73%) samples by the GP5+/6+ PCR and COBAS HPV test. Table 4 shows HPV status in relation to underlying histological diagnosis. HrHPV was present in 12/26 (46%) patients without CIN lesion, 24/36 (67%) CIN1 patients, 36/45 (80%) CIN2 patients, 49/59 (83%) CIN3 patients and 31/43 (72%) patients with miCa. The sensitivity of hrHPV testing for CIN2+ was 79% with a specificity of 42%.

TABLE 4

Cytology according to the Papanicolaou system (Bethesda system) per histological subgroup. Methylation and HPV positivity of the 8 new methylation markers and 4 known markers tested with QMSP in cervical scrapings from patients with CIN0, CIN1, CIN2, CIN3 and (mi)Ca (n = 215).

|  | CIN0 | CIN1 | CIN2 | CIN3 | miCa |
|---|---|---|---|---|---|
| Cytology |  |  |  |  |  |
| Pap2 (ASCUS) | 9/27 (33%) | 9/38 (24%) | 2/45 (4%) | 0 | 0 |
| Pap3A (LSIL) | 18/27 (66%) | 27/38 (71%) | 36/45 (80%) | 18/61 (30%) | 5/44 (11%) |
| Pap3B (HSIL) | 0 | 2/38 (5%) | 6/45 (13%) | 33/61 (54%) | 27/44 (61%) |
| Pap4 (HSIL) | 0 | 0 | 1/45 (2%) | 10/61 (16%) | 8/44 (18%) |
| Pap5 (MiCa) | 0 | 0 | 0 | 0 | 3/44 (7%) |
| Unknown | 0 | 0 | 0 | 0 | 1/44 (2%) |
| New genes |  |  |  |  |  |
| ZSCAN1 | 20/27 (74%) | 28/38 (74%) | 41/45 (91%) | 55/61 (90%) | 44/44 (100%) |
| ST6GALNAC5 | 22/27 (82%) | 33/38 (87%) | 39/45 (84%) | 56/61 (92%) | 41/44 (93%) |
| ANKRD18CP | 3/26 (12%) | 8/36 (22%) | 20/45 (44%) | 33/59 (56%) | 37/43 (86%) |
| CDH6 | 10/26 (39%) | 15/36 (42%) | 25/45 (56%) | 40/59 (68%) | 42/43 (98%) |
| GFRA1 | 1/26 (4%) | 4/36 (11%) | 9/45 (20%) | 23/59 (39%) | 35/43 (81%) |
| GATA4 | 14/26 (54%) | 21/36 (58%) | 35/45 (78%) | 47/59 (80%) | 41/43 (95%) |
| KCNIP4 | 24/27 (89%) | 36/38 (95%) | 44/45 (98%) | 61/61 (100%) | 43/44 (98%) |
| LHX8 | 12/26 (46%) | 20/36 (56%) | 29/45 (64%) | 48/59 (81%) | 41/43 (95%) |
| Known genes |  |  |  |  |  |
| C13ORF18 | 2/27 (7%) | 1/38 (3%) | 9/45 (20%) | 24/61 (39%) | 27/44 (61%) |
| JAM3 | 3/27 (11%) | 3/38 (8%) | 18/45 (40%) | 39/61 (64%) | 37/44 (84%) |
| EPB41L3 | 2/27 (7%) | 12/38 (32%) | 18/45 (40%) | 44/61 (72%) | 41/44 (93%) |
| TERT | 13/27 (48%) | 22/38 (58%) | 29/45 (64%) | 51/61 (84%) | 43/44 (98%) |
| HPV test |  |  |  |  |  |
| HrHPV | 12/26 (46%) | 24/36 (67%) | 36/45 (80%) | 49/59 (83%) | 31/43 (72%) |

For the genes CDH6, GATA4, and LHX8 sensitivity and specificity results were comparable to hrHPV testing with sensitivity for CIN2+ between 73-84% and specificity between 40-60% (Table 5A).

TABLE 5A

Sensitivity and specificity results for CIN2+ and CIN3+ in cervical scrapings from patients referred from population-based screening with an abnormal pap smear (n = 215)

| Gene | Sensitivity CIN2+ | Specificity CIN2+ | Sensitivity CIN3+ | Specificity CIN3+ |
|---|---|---|---|---|
| ZSCAN1 | 93% | 26% | 94% | 19% |
| ST6GALNAC5 | 90% | 15% | 92% | 16% |
| ANKRD18CP | 61% | 82% | 69% | 71% |
| CDH6 | 73% | 60% | 80% | 53% |
| GFRA1 | 46% | 92% | 57% | 87% |
| GATA4 | 84% | 44% | 87% | 35% |
| KCNIP4 | 99% | 8% | 99% | 6% |
| LHX8 | 80% | 40% | 87% | 43% |
| C13ORF18 | 40% | 95% | 49% | 89% |
| EPB41L3 | 69% | 79% | 81% | 71% |
| JAM3 | 63% | 91% | 72% | 78% |
| TERT | 82% | 46% | 90% | 42% |
| hrHPV | 79% | 42% | 78% | 33% |

Table 5B shows sensitivity and specificity for CIN2+ and CIN3+ in scrapings of hrHPV positive women (n=152), which were comparable to the results for the whole group, as shown in Table 5a. The genes ZSCAN1, ST6GALNAC5 and KCNIP4 again showed high sensitivity (≥92%) for the detection of CIN2+, while for CDH6, GATA4, EPB41L3, TERT and ZSCAN16 sensitivity for CIN2+ was between 72-85%. For ANKRD18CP, JAM3, C13ORF18 and GFRA1 sensitivity for CIN2+ was between 43-68%, however these genes showed high specificity between 86-94%. In the current Dutch population based screening program, women with pap2/pap3a (ASCUS/LSIL) scrapings are retested after 6 months with triage testing by hrHPV. Therefore, we also show the results of triage testing by hrHPV and methylation markers in this group (Table 5B). Triage testing by hrHPV shows a sensitivity for CIN2+ of 82% with a specificity of 41%; GATA4, LHX8 and TERT show comparable results.

TABLE 5B

Sensitivity and specificity results for CIN2+ and CIN3+ in scrapings of hrHPV positive women (n = 152) and in scraping of Pap2/Pap3a (ASCUS/LSIL) patients (n = 124).

|  | Sensitivity CIN2+ | Specificity CIN2+ | Sensitivity CIN3+ | Specificity CIN3+ |
|---|---|---|---|---|
| ZSCAN1 | 94% | 36% | 96% | 23% |
| ST6GALNAC5 | 92% | 19% | 94% | 15% |
| ANKRD18CP | 65% | 86% | 74% | 71% |
| CDH6 | 72% | 64% | 83% | 57% |
| GFRA1 | 51% | 92% | 64% | 85% |
| GATA4 | 85% | 47% | 88% | 33% |
| KCNIP4 | 98% | 11% | 99% | 7% |
| LHX8 | 81% | 53% | 91% | 47% |
| C13ORF18 | 43% | 94% | 54% | 88% |
| EPB41L3 | 72% | 78% | 85% | 68% |
| JAM3 | 68% | 94% | 80% | 76% |
| TERT | 81% | 47% | 90% | 43% |
| Only Pap2/3A patients (n = 124) |  |  |  |  |
| ZSCAN1 | 90% | 27% | 87% | 20% |
| ST6GALNAC5 | 90% | 16% | 96% | 15% |
| ANKRD18CP | 38% | 82% | 41% | 75% |
| CDH6 | 58% | 59% | 73% | 56% |
| GFRA1 | 22% | 92% | 32% | 90% |
| GATA4 | 78% | 44% | 77% | 35% |
| KCNIP4 | 98% | 8% | 100% | 6% |
| LHX8 | 70% | 49% | 86% | 46% |
| C13ORF18 | 23% | 95% | 30% | 90% |
| EPB41L3 | 51% | 78% | 74% | 72% |
| JAM3 | 44% | 91% | 57% | 80% |
| TERT | 74% | 48% | 87% | 43% |
| hrHPV | 82% | 41% | 82% | 32% |

Different combinations of genes were analyzed to find the best methylation marker panel with the highest combined sensitivity and specificity. For this analysis a sample was considered positive if either of the genes in the combination tested was positive. By adding more than 3 genes in a combination specificity of the methylation test decreased, with minimal increase in sensitivity. The combinations of genes with the highest combined sensitivity and specificity for CIN2+ was JAM3/ANKRD18CP, C13ORF18/JAM3/ANKRD18CP and JAM3/GFRA1/ANKRD18CP with a sensitivity of 72%, 74% and 73%, which is comparable to hrHPV testing (79%). Specificity of both combinations was 71% and 76%, which is significantly higher than for hrHPV testing (42%) (p≤0.05). Table 6 shows that for all other combinations sensitivities for detecting CIN2+ lesions are between 64-80%, with a combined specificity between 58-88%.

TABLE 6

Combinations of different methylation markers to create a panel of genes most suited as test in scrapings ranked on highest sensitivity (n = 215).

| Gene combination | Sensitivity CIN2+ | Specificity CIN2+ | Sensitivity CIN3+ | Specificity CIN3+ |
|---|---|---|---|---|
| JAM3/CDH6 | 80% | 58% | 85% | 48% |
| ANKRD18CP/CDH6/EPB41L3 | 80% | 55% | 87% | 48% |
| CDH6/EPB41L3 | 78% | 57% | 85% | 50% |
| GFRA1/EPB41L3/CDH6 | 78% | 57% | 85% | 50% |
| ANKRD18CP/CDH6 | 77% | 57% | 83% | 49% |
| GFRA1/ANKRD18CP/CDH6 | 77% | 57% | 83% | 49% |
| JAM3/EPB41L3/ANKRD18CP | 76% | 71% | 84% | 60% |
| C13ORF18/JAM3/ANKRD18CP | 74% | 76% | 80% | 62% |
| ANKRD18CP/EPB41L3 | 74% | 74% | 83% | 64% |
| GFRA1/EPB41L3/ANKRD18CP | 74% | 74% | 84% | 64% |
| C13ORF18/CDH6 | 74% | 58% | 80% | 51% |
| JAM3/GFRA1/ANKRD18CP | 73% | 77% | 80% | 64% |
| C13ORF18/JAM3/EPB41L3 | 73% | 72% | 83% | 64% |
| GFRA1/CDH6 | 73% | 60% | 80% | 53% |
| JAM3/ANKRD18CP | 72% | 79% | 79% | 65% |
| JAM3/EPB41L3 | 72% | 75% | 83% | 66% |
| JAM3/EPB41L3/GFRA1 | 72% | 76% | 83% | 66% |
| GFRA1/EPB41L3 | 69% | 79% | 82% | 71% |
| C13ORF18/EPB41L3 | 69% | 75% | 81% | 68% |
| C13ORF18/JAM3/GFRA1 | 66% | 82% | 77% | 72% |
| JAM3/GFRA1 | 65% | 86% | 76% | 75% |
| C13ORF18/ANKRD18CP | 65% | 79% | 72% | 67% |
| C13ORF18/JAM3 | 64% | 88% | 73% | 76% |
| GFRA1/ANKRD18CP | 64% | 81% | 72% | 69% |

In the hrHPV positive scrapings, the sensitivities and specificities for CIN2+ of the 3 best-performing combinations (JAM3/ANKRD18CP, C13ORF18/JAM3/ANKRD18CP and JAM3/GFRA1/ANKRD18CP) were comparable (sensitivity: 76-77%; specificity: 81-83%) (Table 7) to the total population.

TABLE 7

Combinations of different methylation markers to create a panel of genes most suited as triage test in HPV positive scrapings ranked on highest sensitivity (n = 152).

| Gene combination | Sensitivity CIN2+ | Specificity CIN2+ | Sensitivity CIN3+ | Specificity CIN3+ |
|---|---|---|---|---|
| JAM3/CDH6 | 80% | 64% | 88% | 50% |
| ANKRD18CP/CDH6/EPB41L3 | 79% | 61% | 89% | 51% |
| CDH6/EPB41L3 | 77% | 61% | 88% | 53% |
| GFRA1/EPB41L3/CDH6 | 78% | 61% | 88% | 53% |
| ANKRD18CP/CDH6 | 77% | 61% | 85% | 51% |
| GFRA1/ANKRD18CP/CDH6 | 77% | 61% | 85% | 51% |
| JAM3/EPB41L3/ANKRD18CP | 78% | 72% | 88% | 58% |
| C13ORF18/JAM3/ANKRD18CP | 77% | 81% | 85% | 61% |
| ANKRD18CP/EPB41L3 | 75% | 75% | 86% | 63% |
| GFRA1/EPB41L3/ANKRD18CP | 75% | 75% | 86% | 63% |
| C13ORF18/CDH6 | 73% | 61% | 83% | 54% |
| JAM3/GFRA1/ANKRD18CP | 76% | 81% | 85% | 63% |
| C13ORF18/JAM3/EPB41L3 | 76% | 72% | 86% | 60% |
| GFRA1/CDH6 | 72% | 64% | 83% | 57% |
| JAM3/ANKRD18CP | 76% | 83% | 85% | 64% |
| JAM3/EPB41L3 | 75% | 75% | 86% | 63% |
| JAM3/EPB41L3/GFRA1 | 75% | 75% | 86% | 63% |
| GFRA1/EPB41L3 | 72% | 78% | 85% | 68% |
| C13ORF18/EPB41L3 | 72% | 75% | 85% | 65% |
| C13ORF18/JAM3/GFRA1 | 70% | 86% | 81% | 71% |
| JAM3/GFRA1 | 69% | 89% | 81% | 74% |
| C13ORF18/ANKRD18CP | 68% | 83% | 76% | 67% |
| C13ORF18/JAM3 | 69% | 92% | 80% | 74% |
| GFRA1/ANKRD18CP | 67% | 83% | 76% | 68% |

REFERENCES

1. Peto J, Gilham C, Fletcher O, Matthews F E. *Lancet.* 2004; 364(9430):249-256.
2. Arbyn M, Raifu A O, Weiderpass E, Bray F, Anttila A. *Eur J Cancer.* 2009; 45(15):2640-2648.
3. Cuzick J, Clavel C, Petry K U, et al. *Int J Cancer.* 2006; 119(5):1095-1101.
4. Mayrand M H, Duarte-Franco E, Rodrigues I, et al. *N Engl J Med.* 2007; 357(16):1579-1588.
5. Cox J T, Castle P E, Behrens C M, et al. *Am J Obstet Gynecol.* 2013; 208(3):184.e1-184.e11.
6. Walboomers J M, Jacobs M V, Manos M M, et al. *J Pathol.* 1999; 189(1):12-19.
7. Ronco G, Dillner J, Elfstrom K M, et al. *Lancet.* 2013.
8. Ronco G, Giorgi-Rossi P, Carozzi F, et al. *Lancet Oncol.* 2010; 11(3):249-257.
9. Bulkmans N W, Berkhof J, Rozendaal L, et al. *Lancet.* 2007; 370(9601):1764-1772.
10. Rijkaart D C, Berkhof J, Rozendaal L, et al. *Lancet Oncol.* 2012; 13(1):78-88.
11. Arbyn M, Ronco G, Anttila A, et al. *Vaccine.* 2012; 30 Suppl 5:F88-99.
12. Cuzick J, Arbyn M, Sankaranarayanan R, et al. *Vaccine.* 2008; 26 Suppl 10:K29-41.
13. Kulasingam S L, Hughes J P, Kiviat N B, et al. *JAMA.* 2002; 288(14):1749-1757.
14. Franco E L, Mahmud S M, Tota J, Ferenczy A, Coutlee F. *Arch Med Res.* 2009; 40(6):478-485.
15. Baylin S B, Ohm J E. *Nat Rev Cancer.* 2006; 6(2):107-116.
16. Steenbergen R D, Snijders P J, Heideman D A, Meijer C J. *Nat Rev Cancer.* 2014; 14(6):395-405.
17. Yang N, Nijhuis E R, Volders H H, et al. *Cell Oncol.* 2010; 32(1-2):131-143.
18. Bierkens M, Hesselink A T, Meijer C J, et al. *Int J Cancer.* 2013; 133(6):1293-1299.
19. Hesselink A T, Heideman D A, Steenbergen R D, et al. *Clin Cancer Res.* 2011; 17(8):2459-2465.
20. Lai H C, Lin Y W, Huang R L, et al. *Cancer.* 2010; 116(18):4266-4274.
21. Eijsink J J, Lendvai A, Deregowski V, et al. *Int J Cancer.* 2012; 130(8):1861-1869.
22. Yang N, Eijsink J J, Lendvai A, et al. *Cancer Epidemiol Biomarkers Prev.* 2009; 18(11):3000-3007.
23. Reesink-Peters N, Wisman G B, Jeronimo C, et al. *Mol Cancer Res.* 2004; 2(5):289-295.
24. Laird P W. *Nat Rev Genet.* 2010; 11(3):191-203.
25. Lendvai A, Johannes F, Grimm C, et al. *Epigenetics.* 2012; 7(11):1268-1278.
26. Rauch T A, Pfeifer G P. *Methods.* 2010; 52(3):213-217.
27. van Dongen J J, Langerak A W, Bruggemann M, et al. *Leukemia.* 2003; 17(12):2257-2317.
28. Langmead B, Trapnell C, Pop M, Salzberg S L. *Genome Biol.* 2009; 10(3):R25-2009-10-3-r25. Epub 2009 Mar. 4.
29. De Meyer T, Mampaey E, Vlemmix M, et al. *PLoS One.* 2013; 8(3):e59068.
30. Wisman G B, Nijhuis E R, Hoque M O, et al. *Int J Cancer.* 2006; 119(8):1908-1914.
31. Cui M, Chan N, Liu M, et al. *J Clin Microbiol.* 2014; 52(6):2210-2211.
32. Hawass N E. *Br J Radiol.* 1997; 70(832):360-366.
33. Overmeer R M, Louwers J A, Meijer C J, et al. *Int J Cancer.* 2011; 7(6).
34. Gok M, van Kemenade F J, Heideman D A, et al. *Int J Cancer.* 2012; 130(5):1128-1135.
35. Carozzi F, Confortini M, Dalla Palma P, et al. *Lancet Oncol.* 2008; 9(10):937-945.
36. Carozzi F, Gillio-Tos A, Confortini M, et al. *Lancet Oncol.* 2013; 14(2):168-176.
37. Rijkaart D C, Berkhof J, van Kemenade F J, et al. *Int J Cancer.* 2012; 130(3):602-610.
38. Brentnall A R, Vasiljevic N, Scibior-Bentkowska D, et al. *Int J Cancer.* 2014.
39. Vasiljevic N, Scibior-Bentkowska D, Brentnall A R, Cuzick J, Lorincz A T. *Gynecol Oncol.* 2014; 132(3):709-714.
40. Hansel A, Steinbach D, Greinke C, et al. *PLoS One.* 2014; 9(3):e91905.
41. Verhoef V M, Bosgraaf R P, van Kemenade F J, et al. *Lancet Oncol.* 2014; 15(3):315-322.
42. Sancisi V, Gandolfi G, Ragazzi M, et al. *PLoS One.* 2013; 8(9):e75489.
43. Selamat S A, Chung B S, Girard L, et al. *Genome Res.* 2012; 22(7):1197-1211.

---

The invention claimed is:

1. A method of determining methylation status of marker genes C13ORF18 and ANKRD18CP of a cervical cell comprising using methylation specific PCR primers in methylation specific PCR to determine methylation status of marker genes C13ORF18 and ANKRD18CP of the cervical cell, further comprising optionally detecting methylation status of first marker gene KCNIP4, GFRA1, ST6GALNAC5, CDH6, ZSCAN1, or LHX8 of the cervical cell, or second marker gene JAM3 or EPB41L3 of the cervical cell, wherein methylation of marker genes C13ORF18 and ANKRD18CP indicates a neoplastic cervical cell or a cervical cell predisposed to neoplasia.

2. The method according to claim 1 wherein the cervical cell is within a cervical scraping or a liquid based cytology sample.

3. The method of claim 1 further comprising determining methylation status of JAM3 of the cervical cell.

4. The method of claim 1 wherein the methylation specific PCR primers comprise a first primer comprising sequence CGATGTGGTATTTTCGATTC (SEQ ID NO: 5) and a second primer comprising sequence ACGTGTAAAAAATCGCCAC (SEQ ID NO: 6) for methylation specific PCR amplification of ANKRD18CP.

5. The method of claim 1 comprising using a probe for C13ORF18 and a probe for ANKRD18CP.

6. The method of claim 5 further comprising using a probe for JAM3.

7. The method of claim 5 comprising using a probe comprising sequence AGGAGCGTTTGGTTTAGGCGTTTTTCG (SEQ ID NO: 19).

8. The method of claim 2 wherein the cervical scraping is a self-collected vaginal swab.

9. The method of claim 1 wherein the methylation specific PCR is quantitative methylation specific PCR.

10. The method of claim 1 wherein the methylation specific PCR primers comprise a first primer comprising sequence TTGTTGGTATTCGTTTGTTC (SEQ ID NO: 1) and a second primer comprising sequence ACGCGACCGAACGATATT (SEQ ID NO: 2) for methylation specific PCR amplification of ZSCAN1.

11. The method of claim 1 wherein the methylation specific PCR primers comprise a first primer comprising sequence GTAGTTGCGGATGGAGGTTC (SEQ ID NO: 3) and a second primer comprising sequence CTAACTACGCTCACCCTCCG (SEQ ID NO: 4) for methylation specific PCR amplification of ST6GALNAC5.

12. The method of claim 1 wherein the methylation specific PCR primers comprise a first primer comprising sequence GGGCGGCGTTGTTGTC (SEQ ID NO: 7) and a second primer comprising sequence CCAACCCCACGACGAATC (SEQ ID NO: 8) for methylation specific PCR amplification of CDH6.

13. The method of claim 1 wherein the methylation specific PCR primers comprise a first primer comprising sequence TAGGGGGAATCGATGTTTC (SEQ ID NO: 9) and a second primer comprising sequence GAATCCTAAACACCGAACGA (SEQ ID NO: 10) for methylation specific PCR amplification of GFRA1.

14. The method of claim 1 wherein the methylation specific PCR primers comprise a first primer comprising sequence GGTCGGGTTAATTCGGTC (SEQ ID NO: 11) and a second primer comprising sequence CCTCGACAAAACTCAAAACG (SEQ ID NO: 12) for methylation specific PCR amplification of GATA4.

15. The method of claim 1 wherein the methylation specific PCR primers comprise a first primer comprising sequence GGGACGTAGGGTGTAGAAGC (SEQ ID NO: 13) and a second primer comprising sequence AAACTCTCGCTCCCAACG (SEQ ID NO: 14) for methylation specific PCR amplification of KCNIP4.

16. The method of claim 1 wherein the methylation specific PCR primers comprise a first primer comprising sequence TATTTTTTTCGTAGCGGATC (SEQ ID NO: 15) and a second primer comprising sequence ACGAAAAACCAAATTCTACG (SEQ ID NO: 16) for methylation specific PCR amplification of LHX8.

* * * * *